(12) United States Patent
Obata

(10) Patent No.: US 7,662,090 B2
(45) Date of Patent: Feb. 16, 2010

(54) ENDOSCOPE SYSTEM

(75) Inventor: Mitsuo Obata, Hachioji (JP)

(73) Assignee: Olympus Corporation (JP)

( * ) Notice: Subject to any disclaimer, the term of this patent is extended or adjusted under 35 U.S.C. 154(b) by 644 days.

(21) Appl. No.: 11/052,569

(22) Filed: Feb. 7, 2005

(65) Prior Publication Data

US 2006/0178558 A1 Aug. 10, 2006

(51) Int. Cl.
*A61B 1/00* (2006.01)
*A61B 1/04* (2006.01)

(52) U.S. Cl. ...................... 600/118; 600/109

(58) Field of Classification Search ............. 600/101, 600/109, 113, 117, 118, 160
See application file for complete search history.

(56) References Cited

U.S. PATENT DOCUMENTS

| | | | |
|---|---|---|---|
| 5,196,928 A * | 3/1993 | Karasawa et al. | 348/65 |
| 6,636,254 B1 * | 10/2003 | Onishi et al. | 348/65 |
| 7,179,222 B2 * | 2/2007 | Imaizumi et al. | 600/109 |
| 2004/0082834 A1 * | 4/2004 | Onishi et al. | 600/118 |
| 2005/0020878 A1 * | 1/2005 | Ohnishi et al. | 600/117 |
| 2005/0033117 A1 * | 2/2005 | Ozaki et al. | 600/109 |
| 2005/0054896 A1 * | 3/2005 | Konishi | 600/118 |

FOREIGN PATENT DOCUMENTS

| | | |
|---|---|---|
| JP | 07-250813 | 10/1995 |
| JP | 2001-136515 | 5/2001 |
| JP | 2001-218735 | 8/2001 |
| JP | 2001-275952 | 10/2001 |
| JP | 2002-010974 | 1/2002 |

OTHER PUBLICATIONS

Japanese Office Action mailed Jun. 23, 2009 in corresponding Japanese Patent Application No. 2003-190586 (Japanese language).
Office Action issued by the Japanese Patent Office on Oct. 20, 2009 in connection with corresponding Japanese Patent Application No. 2003-190586.

* cited by examiner

*Primary Examiner*—John P Leubecker
*Assistant Examiner*—Philip R Smith
(74) *Attorney, Agent, or Firm*—Ostrolenk Faber LLP

(57) ABSTRACT

An endoscope system includes an endoscope switching device 3 to which a plurality of endoscope devices are simultaneously connected, and an endoscope control device which controls the plurality of endoscope devices via the endoscope switching device 3. The endoscope switching device 3 includes an image combining circuit 73 which combines video signals outputted from the plurality of endoscope devices and creates a combined image signal for simultaneously displaying the plurality of endoscope images, and a switching device control unit 75 which controls the image combining circuit 73. The switching device control unit 75 controls the operation for distributing a control command from a remote controller or PC to the corresponding endoscope device based on a character code sent from a system control unit in the endoscope control device. Simultaneously, the switching device control unit 75 controls the image combining circuit 73 via a serial I/F.

15 Claims, 11 Drawing Sheets

ENDOSCOPE SYSTEM

This Application claim benefit of Japanese Patent Application No. 2003-190586 filed in Japan on Jul. 2, 2003, the contents of which are incorporated by this reference.

BACKGROUND OF THE INVENTION

1. Field of the Invention

The present invention relates to an endoscope system which simultaneously uses a plurality of endoscope devices.

2. Description of the Related Art

Conventionally, an endoscope device has widely been used. In the medical field, the endoscope device observes the organ in the body cavity by inserting an elongated inserting portion into the body cavity, and performs various therapeutic treatments by using a treatment tool inserted in a treatment tool channel if necessary. Further, in the industrial field, the endoscope device inspects and treats the inner scratch or corrosion of a boiler, turbine, engine, and chemical plant.

Furthermore, the endoscope device is used as a monitor device. In this case, a plurality of endoscope devices form the endoscope system to view images picked-up at many points.

The above-mentioned endoscope system is proposed, for example, in Japanese Unexamined Patent Application Publication No. 2001-218735.

SUMMARY OF THE INVENTION

According to the present invention, an endoscope system comprises: an image combining unit which combines video signals outputted from a plurality of endoscope devices and simultaneously displays a plurality of endoscope images.

Further, an endoscope system comprises: an endoscope switching device, to which a plurality of endoscope devices are simultaneously connected and which combines video signals outputted from the plurality of endoscope devices; a selecting unit which selects a desired one of the plurality of endoscope devices, as a control target; and a selecting and display portion which identifies the corresponding endoscope device as the control target.

DESCRIPTION OF THE PREFERRED EMBODIMENTS

Hereinbelow, embodiments of the present invention will be described with reference to the drawings.

First Embodiment

Figure 1:
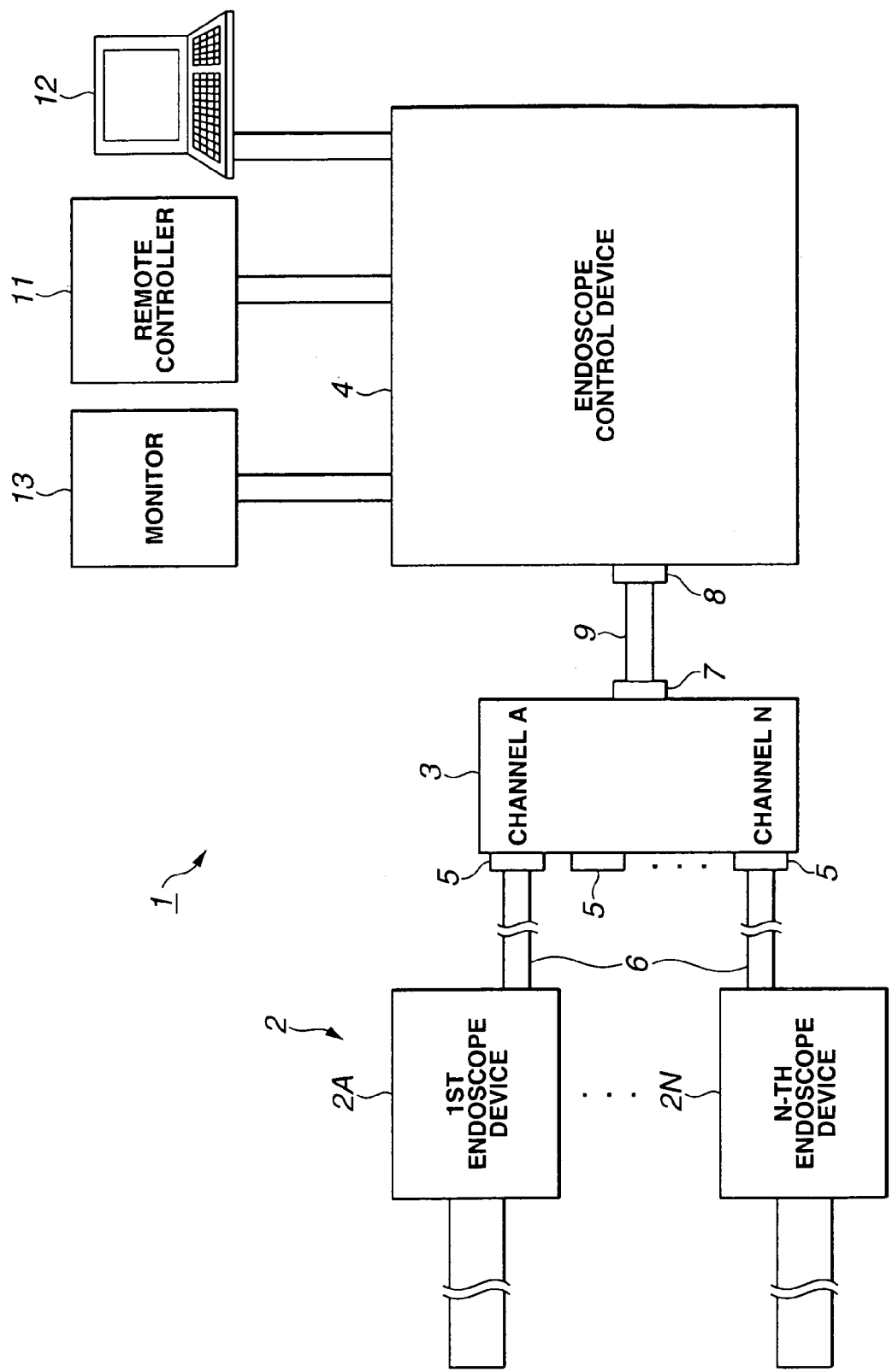
FIG. 1 is a block diagram showing an entire structure of an endoscope system according to a first embodiment.

FIGS. 1 to 9 show a first embodiment of the present invention. Referring to FIG. 1, an endoscope system 1 according to the first embodiment of the present invention mainly comprises: an endoscope switching device 3 to which 1st to N-th endoscope devices 2 are simultaneously connected; and an endoscope control device 4 which controls the 1st to N-th endoscope devices 2 via the endoscope switching device 3.

The endoscope switching device 3 comprises a plurality of connector portions 5 to which the 1st to N-th endoscope devices 2 are connected. The 1st to N-th endoscope devices 2 are detachably connected to the connector portions 5 via a universal cable 6. Incidentally, as shown in FIG. 1, channels A to N denote connecting lines between the endoscope switching device 3 and the 1st to N-th endoscope devices 2.

The endoscope switching device 3 is detachably connected to the endoscope control device 4 via connectors 7 and 8 by using a connecting cable 9. A remote controller 11 is connected to the endoscope control device 4 and the remote controller 11 instructs operations. Further, a PC (personal computer) 12 is connected to the endoscope control device 4, and the PC 12 instructs operations.

The endoscope control device 4 controls the endoscope switching device 3 based on the operating instruction from the remote controller 11 or PC 12 to combine video signals outputted from the 1st to N-th endoscope devices 2, simultaneously displays an endoscope image captured from the 1st to N-th endoscope devices 2 on a monitor 13, and controls the desired endoscope device.

Figure 2:
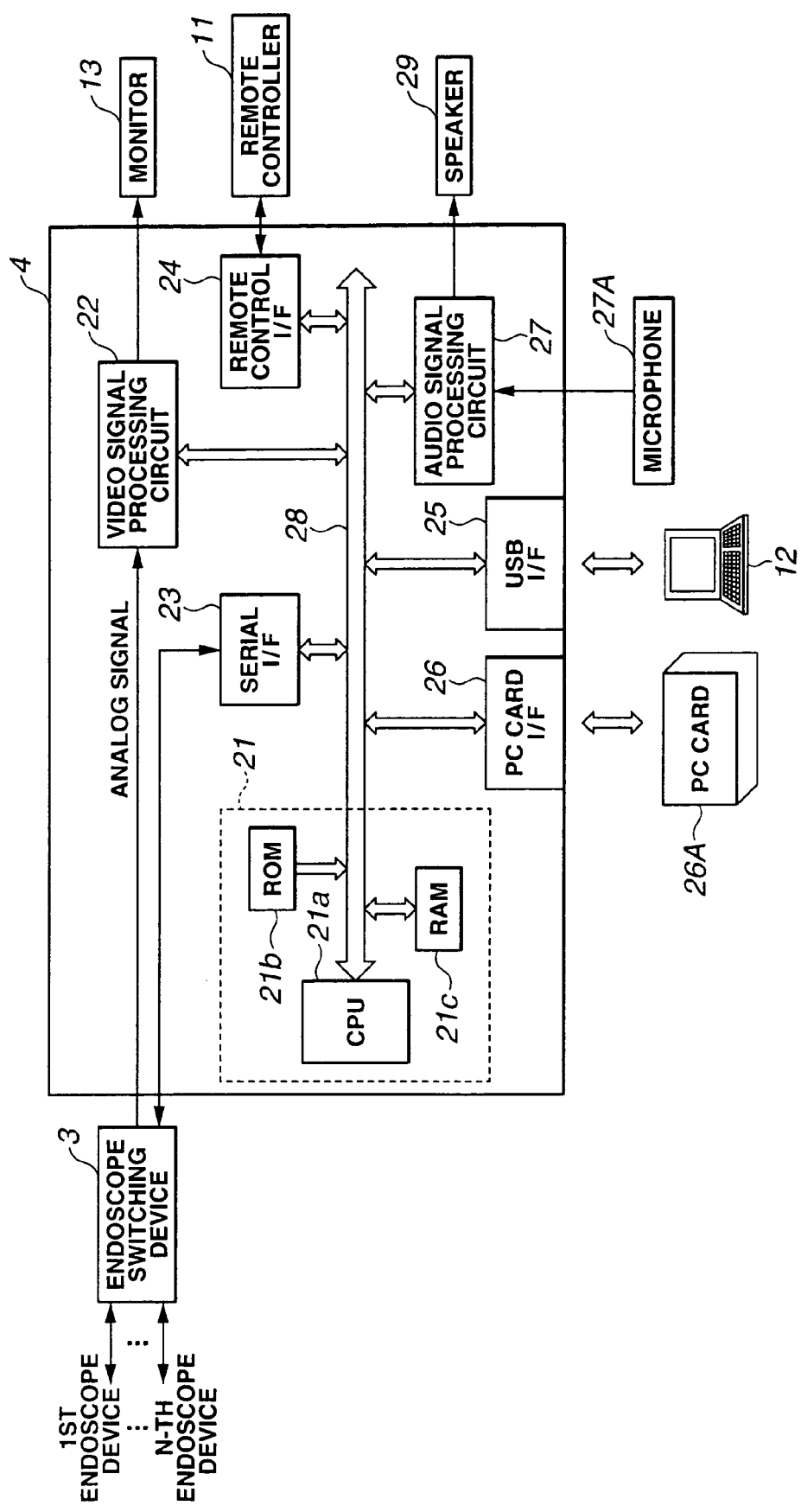
FIG. 2 is a circuit block diagram showing the inner structure of an endoscope control device.

First, the inner structure of the endoscope control device 4 will be described. Referring to FIG. 2, the endoscope control device 4 comprises a system control unit 21 which centrally controls various operations of the entire endoscope system. The endoscope control device 4 comprises: a video signal processing circuit 22 which processes an analog video signal outputted from the endoscope switching device 3 and outputs the processed signal to the monitor 13; a serial interface (hereinafter, serial I/F) 23 which communicates data with the 1st to N-th endoscope devices 2 via the endoscope switching device 3; a remote controller I/F 24 which communicates data with the remote controller 11; a USB (Universal Serial Bus) I/F 25 which communicates data with the PC 12; a PC card I/F 26 which writes/reads image data to a compact-flash-type PC card 26A serving as a storage medium; and an audio signal processing circuit 27 which processes an analog audio signal inputted from a microphone 27A and captures the processed analog audio signal. The various processing circuits and I/Fs 22 to 27 are under the control of operations of the system control unit 21 by the connection to a bus 28.

The endoscope control device 4 is connected to a speaker 29 to generate sound captured by the microphone 27A or collected sound. The microphone 27A may be arranged to the remote controller 11. In this case, the audio signal processing circuit 27 is connected to the remote controller I/F 24. Further, the endoscope control device 4 may include the microphone 27A at the tip of an inserting portion of the endoscope device 2, thereby collecting an endoscope moving image and sound and generating the sound from the speaker 29 via the audio signal processing circuit 27.

The system control unit 21 comprises: a CPU 21a; a ROM 21b; and a RAM 21c. The CPU 21a is main control means which controls portions of the endoscope control device 4. The ROM 21b stores a program for operating the CPU 21a. The RAM 21c is used as a work area of the CPU 21a or a temporary storage area of various data.

The CPU 21a of the system control unit 21 sends, to the endoscope switching device 3, a character code generated based on a control command format, which will be described later. The endoscope switching device 3 controls a switching device control unit, which will be described later, to distribute a control command from the remote controller 11 or PC 12 to the 1st to N-th endoscope devices 2.

Figure 3:
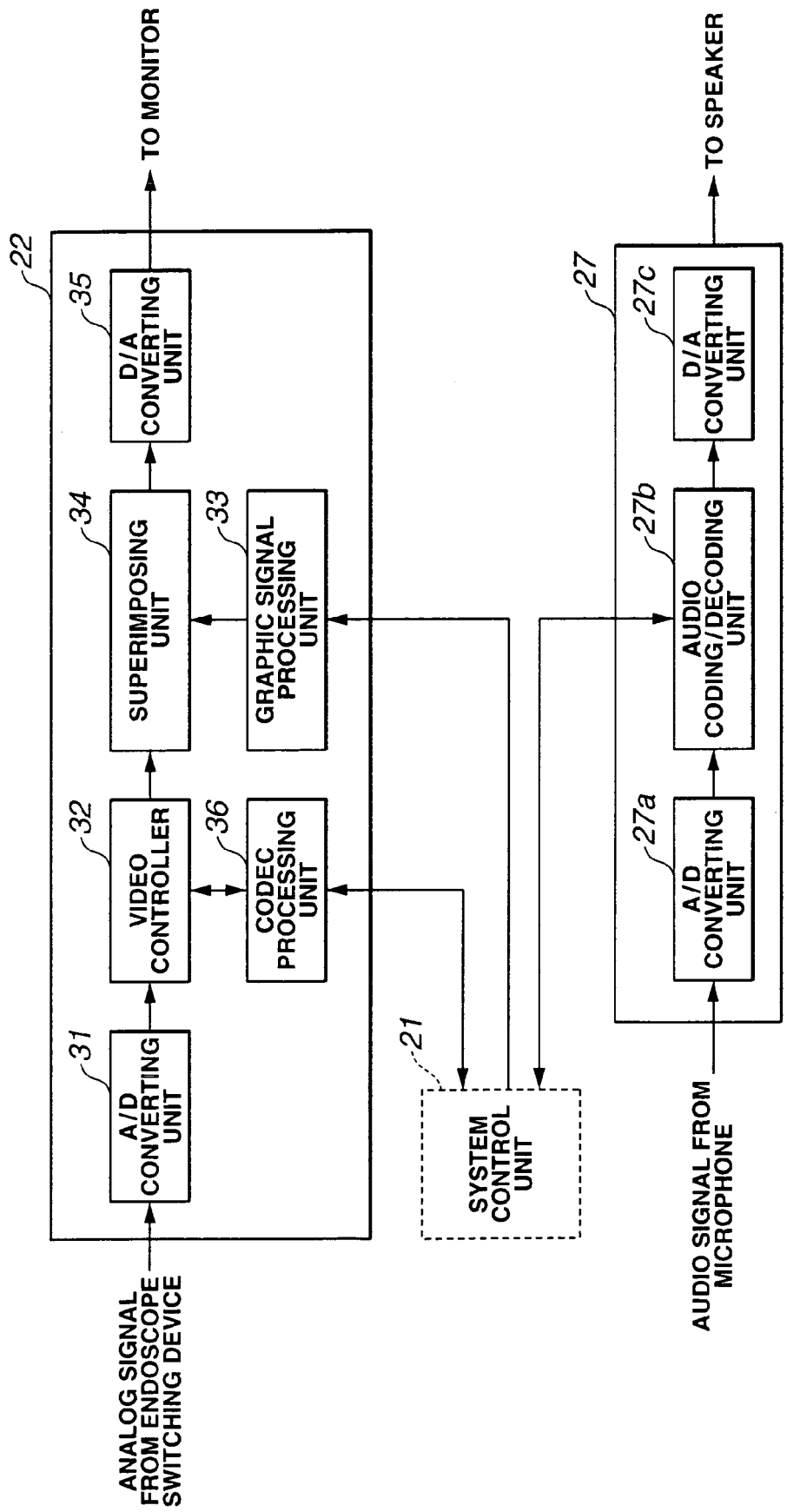
FIG. 3 is a circuit block diagram showing the inner structures of a video signal processing circuit and an audio signal processing circuit shown in FIG. 2.

Referring to FIG. 3, the video signal processing circuit 22 comprises: an A/D converting unit 31 which A/D converts an analog video signal from the endoscope switching device 3; a video controller 32 which stores a digital signal after A/D conversion into a frame memory (not shown) and performs image processing such as trimming and edge emphasis; a graphic signal processing unit 33 which processes a graphic signal for displaying additional information such as font and menu created by the CPU 21a of the system control unit 21 and the date to create a graphic video signal; a superimposing unit 34 which superimposes the created graphic video signal to a video signal from the video controller 32; and a D/A converting unit 35 which D/A converts the superimposed digital signal and outputs the D/A converted signal to the monitor 13.

The frame memory of the video controller 32 is controlled by the system control unit 21. Upon recording the video signal, the data stored in the frame memory is sent via the bus 28 and is inputted to the PC card 26A via the system control unit 21. The video signal is read from the PC card 26A via a reversing route of the foregoing.

Upon recording or playing the image, the video signal processing circuit 22 enables a codec processing unit 36 to compress/decompress the data. In this case, the codec processing unit 36 uses JPEG (Joint Photograph Expert Group) for a still image and motion JPEG or MPEG (Moving Picture Expert Group) for a moving image.

The audio signal processing circuit 27 comprises: an A/D converting unit 27a which A/D converts an analog audio signal inputted from the microphone 27A into a digital audio signal; a audio encoding/decoding unit 27b which encodes or decodes the digital audio signal; and a D/A converting unit 27c which D/A converts the digital audio signal.

The analog audio signal from the microphone 27A is A/D converted and is encoded as audio data. Then, the processed data is stored in the PC card 26A via the PC card I/F 26 under the control of the system control unit 21. The audio data stored in the PC card 26A is decoded and is D/A converted and thus is generated as sound from the speaker 29.

Next, a description is given of the detailed structures of the endoscope switching device 3 and the endoscope device 2. According to the first embodiment, for a belief description, the first and second endoscope devices are connected as the 1st to N-th endoscope devices 2.

Figure 4:
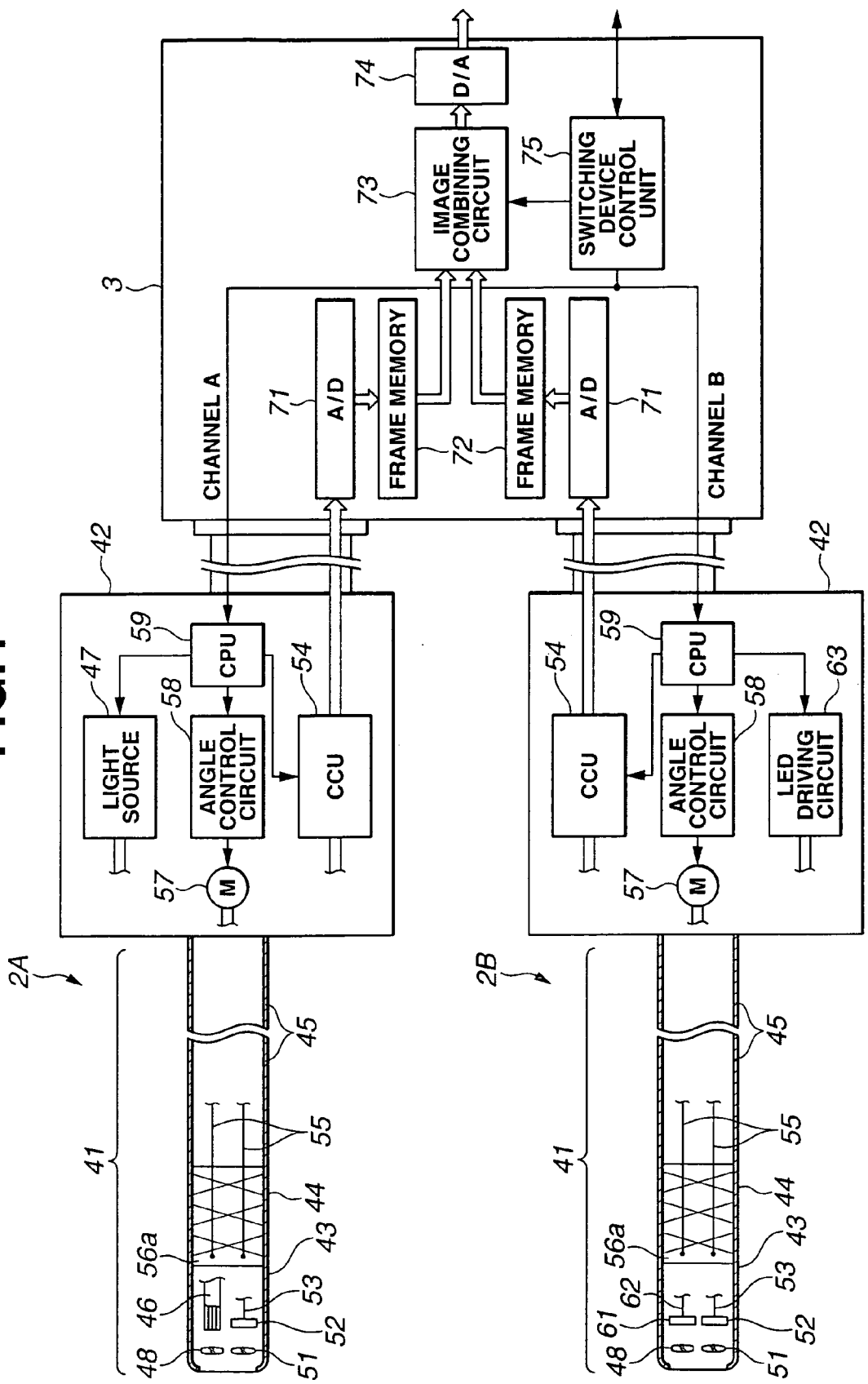
FIG. 4 is an explanatory diagram showing the inner structures of an endoscope switching device and first and second endoscope devices.

Referring to FIG. 4, a first endoscope device 2A and a second endoscope device 2B are connected to the endoscope switching device 3. The first endoscope device 2A comprises: an elongated and flexible inserting portion 41; and a device main body 42 arranged to the base end of the inserting portion 41.

The inserting portion 41 comprises: a hard distal-end portion 43 arranged to the tip; a bending portion 44 which is flexible and is arranged to the base end of the distal-end portion 43; and a flexible tube portion 45 which is long and flexible and is arranged to the base end of the bending portion 44.

A light guide 46 for transmitting illuminating light is inserted in the inserting portion 41. The light guide 46 transmits the illuminating light from a light source 47 arranged in the device main body 42 at the base end of the light source 47. The illuminating light transmitted from the light guide 46 illuminates a subject via an illuminating optical system 48 from an illuminating window (not shown) fixed to an edge surface of the distal-end portion 43 of the inserting portion.

An image of the illuminated subject is captured from an observing window (not shown) arranged adjacently to the illuminating window. The captured subject image is condensed by an objective optical system 51 arranged at the back of the illuminating window. The subject image is picked-up by an image pickup device 52 such as a CCD (charge coupled device) arranged at the condensing position of the objective optical system 51 and then is photoelectrically converted into an image pickup signal. The image pickup signal is transmitted via a signal cable 53 extended from the image pickup device 52, and is outputted to a CCU (camera control unit) 54 in the device main body 42. The CCU 54 processes the image pickup signal from the image pickup device 52, creates a standard video signal, and outputs the created signal to the endoscope switching device 3.

A wire 55 for bending operation for bending the bending portion 44 in the horizontal and vertical directions of the observing field-of-view is inserted in the inserting portion 41. The distal end of the wire 55 for bending operation is fixed and is held at most front bending pieces 56a corresponding to the positions in the horizontal and vertical directions of the bending portion 44 by the brazing or the like. The wire 55 for bending operation electrically bends the bending portion 44 by the traction and loosing with a bending motor 57 arranged in the device main body 42. The driving of bending motor 57 is controlled by an angle control circuit 58.

In the device main body 42, the light source 47, the angle control circuit 58, and the CCU 54 are controlled by a CPU 59. Specifically, the CPU 59 controls the on/off operation of the light source 47 and the stop operation. Further, the CPU 59 sets a driving condition of the bending motor 57 for the angle control circuit 58. Furthermore, the CPU 59 sets the electric zoom operation, brightness, dynamic range of the CCU 54. Then, the CPU 59 is controlled by the system control unit 21 of the endoscope control device 4 via the switching device control unit of the endoscope switching device 3.

The first endoscope device 2A is directly connected to the monitor 13 to supply the video signal from the CCU 54 to the monitor 13 and display the endoscope image on a display screen of the monitor 13.

The second endoscope device 2B has the distal-end portion 43 having an LED 61 serving as a light source and the device main body 42 having an LED driving circuit 63 for driving the LED 61 via a signal line 62. Except for the above-mentioned structure, the second endoscope device 2B has the same structure as that of the first endoscope device 2A, and a description thereof is omitted.

The endoscope switching device 3 comprises: an A/D converting unit 71 which A/D converts analog video signals outputted from the first endoscope device 2A and second endoscope device 2B; a frame memory 72 which temporarily stores the A/D converted digital signals; an image combining circuit 73 which combines the digital signals stored in the frame memory 72 and creates a combined image signal for enabling the simultaneous display operation of a plurality of endoscope images; a D/A converting unit 74 which D/A converts the image combined signal and outputs the D/A converted signal to the endoscope control device 4; and a switching device control unit 75 which controls the image combining circuit 73.

According to the first embodiment, the first endoscope device 2A and the second endoscope device 2B are connected to the endoscope switching device 3 and therefore the endoscope switching device 3 has two sets of the A/D converting unit 71 and the frame memory 72.

Figure 5:
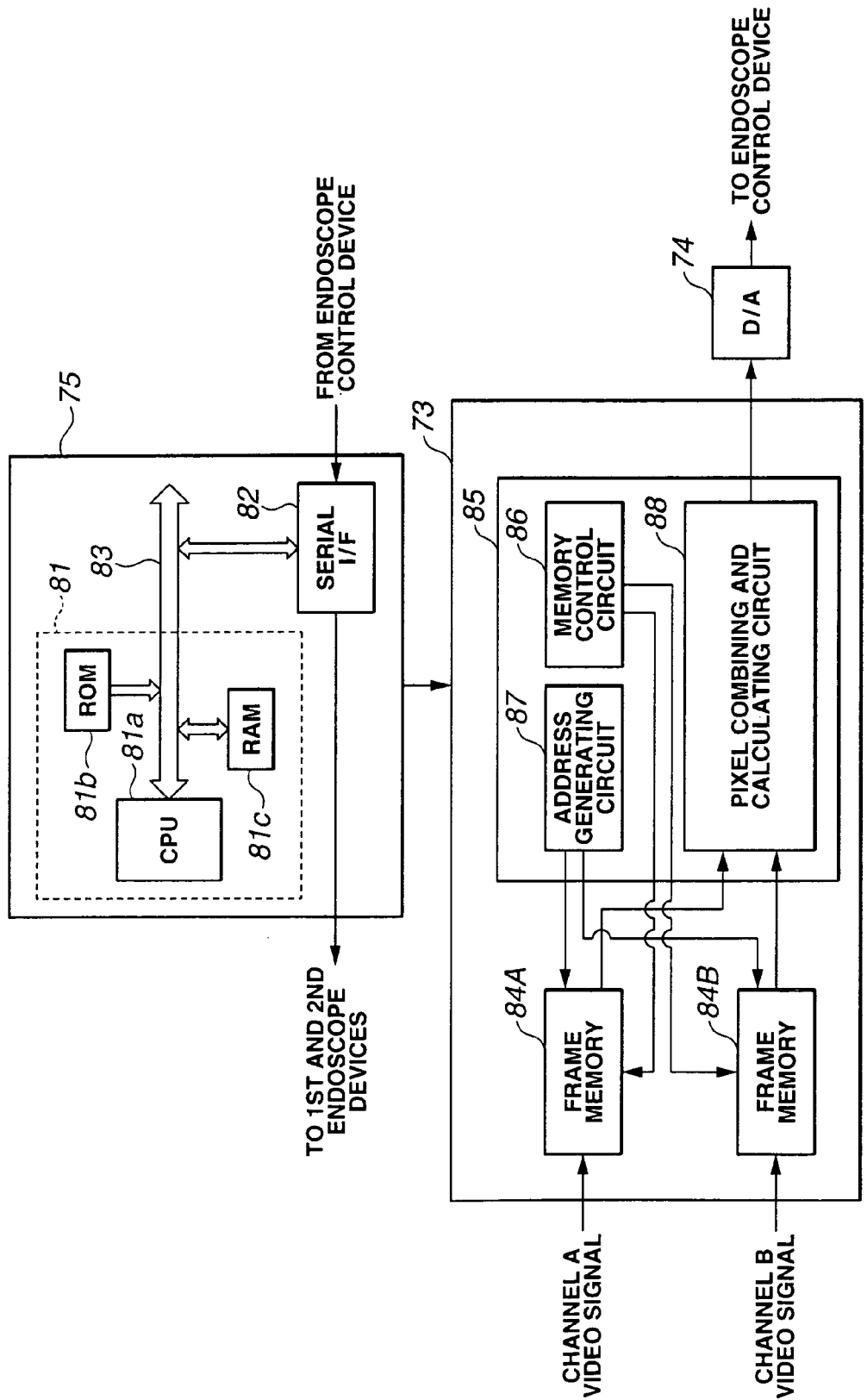
FIG. 5 is a circuit block diagram showing the inner structures of a switching control device and an image combining circuit shown in FIG. 4.

Referring to FIG. 5, the switching device control unit 75 comprises: a control unit 81 which concentratedly controls various operations of the entire device; and a serial I/F 82 which communicates the data with the first endoscope device 2A and second endoscope device 2B. The control unit 81 is connected to the serial I/F 82 via a bus 83. The control unit 81 comprises: a CPU 81*a*; a ROM 81*b*; and a RAM 81*c*. The CPU 81*a* is main control means which controls the units of the endoscope switching device 3. The ROM 81*b* stores a program for operating the CPU 81*a*. The RAM 81*c* is used as a work area of the CPU 81*a* or a temporary storage area of various data.

The CPU 81*a* of the switching device control unit 75 controls the operation for distributing a control command from the remote controller 11 or PC 12 to the first endoscope device 2A and the second endoscope device 2B based on a character code sent from (the CPU 21*a* of) the system control unit 21 of the endoscope control device 4. Simultaneously, the CPU 81*a* of the switching device control unit 75 controls the image combining circuit 73 via the serial I/F 82.

The image combining circuit 73 comprises: frame memories 84A and 84B which temporarily store the digital signals from the first endoscope device 2A and second endoscope device 2B stored in the frame memory 72 in each of even/odd field under the control of the CPU 81*a* of the switching device control unit 75 via the serial I/F 82; and a pixel combining unit 85 which combines the digital signal stored in the frame memories 84A and 84B for each pixel.

The pixel combining unit 85 comprises: a memory control circuit 86 which generates an enable signal (or disable signal) for setting valid/invalid of the digital signal stored in the frame memories 84A and 84B; an address generating circuit 87 which generates address signals from the frame memories 84A and 84B, which are set to valid/invalid by the memory control circuit 86; and a pixel combining and calculating circuit 88 which combines, for each pixel, the digital signals stored in the frame memories 84A and 84B based on the enable signal from the memory control circuit 86 and the address signal from the address generating circuit 87.

When the first and second endoscope images are simultaneously displayed in the horizontal direction (refer to FIG. 8) and the number of pixels on one screen is (640×480) dots, the pixel combining unit 85 sets, to valid, (the digital signal stored in) the frame memory 84A of the channel A (first endoscope image) until the number of pixels in the X-direction (horizontal direction) is 0 to 319 dots so as to combine the images and create a combined image signal. Until the number of pixels on one screen is (320×639) dots, the pixel combining unit 85 sets, valid, (the digital signal stored in) the frame memory 84B of the channel B (second endoscope image).

The created combined image signal is D/A converted by the D/A converting unit 74 as mentioned above. Then, the D/A converted signal is outputted to the video signal processing circuit 22 in the endoscope control device 4.

In the above-mentioned image combination, (the CPU 21*a* of) the endoscope control device 4 controls (the CPU 81*a* of) the endoscope switching device 3 based on an operating instruction of the remote controller 11 or PC 12 to combine the video signals outputted from the first endoscope devices 2A and 2B and display the combined video signal on the monitor 13, and further controls the desired endoscope device.

In this case, (the CPU 21*a* of) the endoscope control device 4 sends a command to (the CPU 81*a* of) the endoscope switching device 3 in accordance with the operating command from the remote controller 11 or PC 12.

Figure 6:
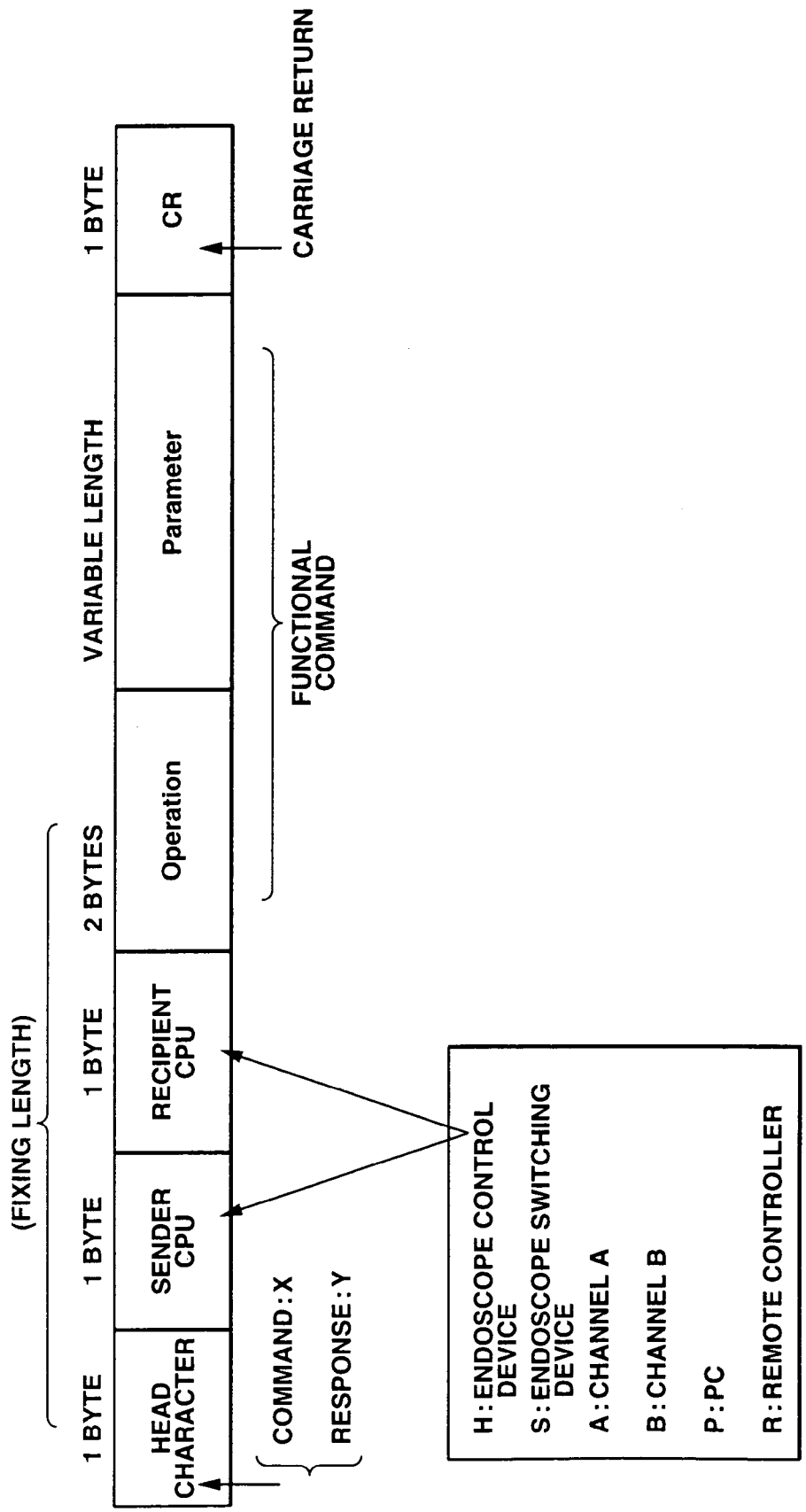
FIG. 6 is a schematic diagram showing a control command format.

The character code created by (the CPU 21*a* of) the endoscope control device 4 is created based on a control command format shown in FIG. 6. Referring to FIG. 6, the control command format comprises, starting from the head, "head character", "recipient CPU", "sender CPU", "operation", "parameter", and "carriage return". The "head character" has the capacity of one byte, and is a character code indicating the command as "X" and the response to the command as "Y". The "recipient CPU" has the capacity of one byte, and a character code indicating the unit serving as the sender of the command. The "sender CPU" has the capacity of one byte and a character code indicating the unit serving as the sender of the command. The "operation" has the capacity of two bytes, and is a character code indicating a function controlled by two characters. For example, reference symbol AX denotes the angle coordinate of the bending portion 44. The fixed length contains the "head character" to "operation".

The "parameter" has the variable capacity and is a character code indicating an operation parameter. The "operation" and the "parameter" form a functional command for controlling the CCU 54, for example, the angle control circuit 58, and the LED driving circuit 63.

The functional command is formed, for example, as shown in Table 1.

TABLE 1

| OPERATION | FUNCTION | PARAMETER LENGTH | BYTE | PARAMETER |
|---|---|---|---|---|
| JT | INCLINATION DATA OF JOYSTICK | 6 | 1 | Y |
|  |  |  | 2 | DIRECTION |
|  |  |  | 3 | (000–3FF) |
|  |  |  | 4 | X |
|  |  |  | 5 | DIRECTION |
|  |  |  | 6 | (000–3FF) |
| RB | REMOTE CONTROL BUTTON | 2 | 1 | CODE SWITCH 0 CHANNEL 1 CONTROL |

TABLE 1-continued

| OPERATION | FUNCTION | PARAMETER LENGTH | BYTE | PARAMETER |
|---|---|---|---|---|
| | | | 2 | LED |
| | | | 3 | MENU |
| | | | 4 | FREEZE |
| | | | 5 | REC |
| | | | 6 | INDEX |
| | | | 2 | 1: MAKE 0: BREAK |

The functional commands shown in Table 1 indicate the operation of the remote controller 11.

the "operation" indicates, as "JT", inclination data of the joystick, and further indicates, as "RB", the remote control button.

The "parameter" indicates the inclination data of the joystick containing 6 bytes and the operation of the remote control button containing 2 bytes.

The inclination data of the joystick is expressed by hexadecimal, and has the former 3 bytes (000 to 3FF) in the Y direction and the latter 3 bytes (000 to 3FF) in the X direction. The inclination data of the joystick is sent by 1024 steps (hexadecimal) in the X and Y directions.

In the operation of the remote control button, the first byte indicates a switch (button) function (type) and the second byte indicates the operating state of the switch.

The remote controller 11 has various switches (buttons), which will be described later, corresponding to codes of the switches. When any of the switches is pressed, "MAKE" is assigned to the second byte. When the pressed switch is released, "BREAK" is assigned to the second byte.

The "carriage return" has the capacity of one byte, and is a character code indicating the end of code.

(The CPU 21*a* of) the endoscope control device 4 performs "inquiry" of the poling for checking the connection to (the CPU 81*a* of) the endoscope switching device 3 or of the check of setting of the PC 12, the parameter is sent "?". In this case, the "parameter" is indicated as "XAS . . . ?". For "response" serving as the answer from (the CPU 81*a* of) the endoscope switching device 3 to "inquiry", the "head character" is indicated as "Y".

Figure 7:
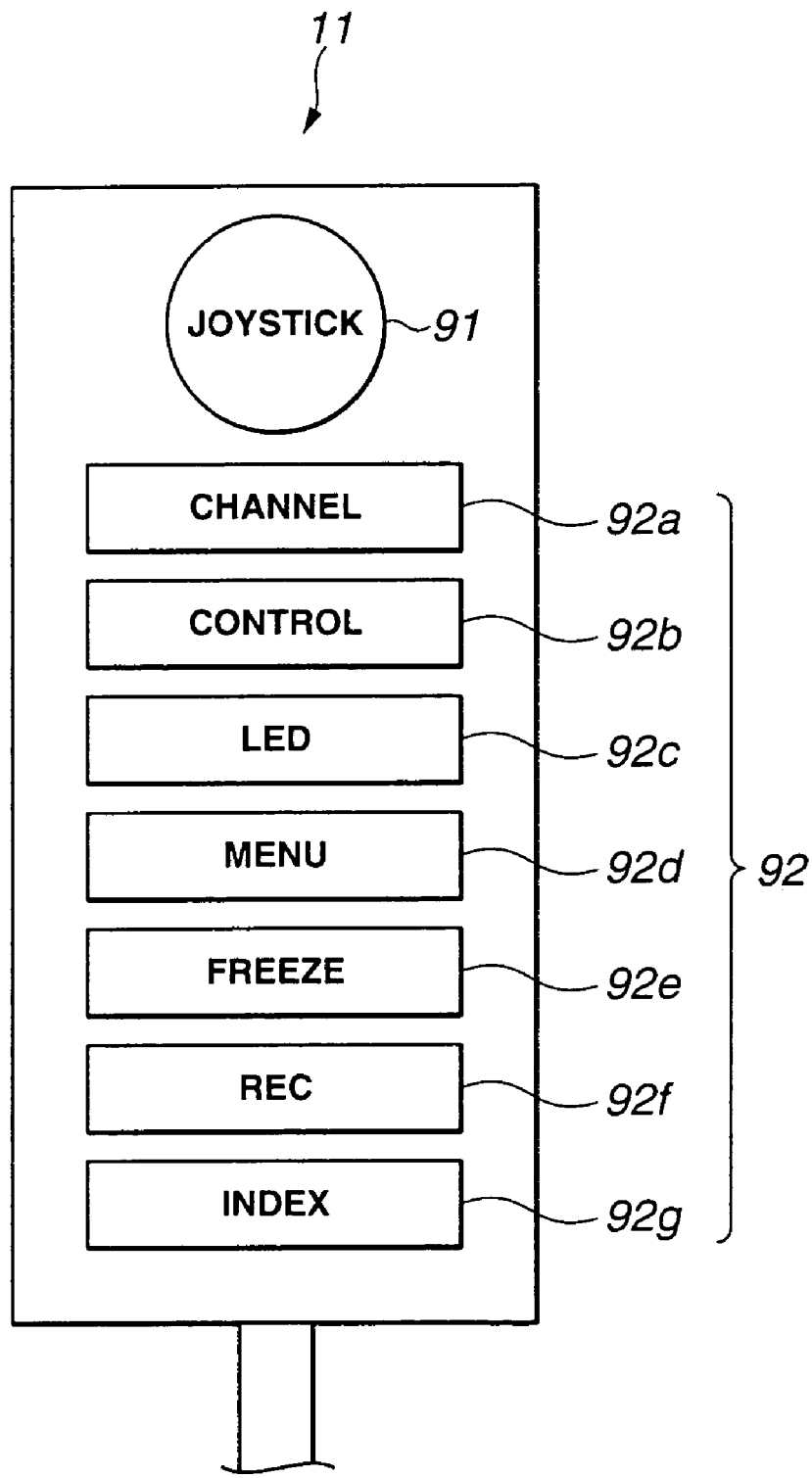
FIG. 7 is a schematic view showing the structure of a remote controller.

Next, the structure of the remote controller 11 will be described. Referring to FIG. 7, the remote controller 11 has a joystick 91 for instructing the bending operation of the bending portion 44 of the inserting portion 41, and switches (buttons) 92. The remote controller 11 may have a track ball, in place of the joystick 91.

The switches (buttons) 92 include: a channel switch 92*a* for operating the channels, which will be described later; a control switch 92*b* serving as selecting means for selection, which will be described later; an LED switch 92*c* for turning on/off the LED 61 and adjusting the intensity of illumination; a menu switch 92*d* for displaying a menu screen; a freeze switch 92*e* for displaying a still image; a record switch 92*f* for recording the image; and an index switch 92*g* for displaying the recorded image as a thumbnail image.

The operation of the endoscope system 1 with the above-mentioned structure will be described. As mentioned above, in the endoscope system 1, the first endoscope device 2A and the second endoscope device 2B are simultaneously connected to the endoscope switching device 3, and the endoscope control device 4 controls the endoscope devices 2A and 2B via the endoscope switching device 3 for endoscope examination.

The first endoscope device 2A and the second endoscope device 2B obtain the first and second endoscope images. The endoscope switching device 3 combines the video signals from the first endoscope device 2A and the second endoscope device 2B, and outputs the combined signal to the endoscope control device 4. The endoscope control device 4 processes the video signal from the endoscope switching device 3, and displays the combined image on the monitor 13.

The remote controller 11 is operated and then (the CPU 21*a* of) the endoscope control device 4 sends the character code created based on the above control command format to (the CPU 81*a* of) the endoscope switching device 3 in accordance with the operating command (functional command) from the remote controller 11. In this case, (the CPU 21*a* of) the endoscope control device 4 changes the sender CPU to the "endoscope control device 4" and the recipient CPU to the "endoscope switching device".

(The CPU 81*a* of) the endoscope switching device 3 sends the command to the currently-selected "endoscope device", namely, the channel A or channel B. In this case, the sender CPU is changed to the "endoscope switching device", and the recipient CPU is changed to the selected endoscope device. The CPU 59 of the corresponding endoscope device controls the CCU 54, the angle control circuit 58, and the LED driving circuit 63 in accordance with the parameter of the command sent from (the CPU 81*a* of) the endoscope switching device 3.

If the parameter indicates the "inclination data of the joystick 91", the CPU 59 of the endoscope device D/A converts the digital value indicated by the data and outputs a motor driving voltage to the angle control circuit 58, thereby controlling the angle of the bending portion 44.

If the parameter indicates the "press FREEZE switch", the CPU 59 of the endoscope device outputs a freeze signal to the CCU 54, and controls a frame memory (not shown) of the CCU 54 to freeze the image.

If the parameter indicates "press LED switch", the CPU 59 of the endoscope device outputs, a value of the second bit shown in Table 2, to the LED driving circuit 63. Then, the LED driving circuit 63 decodes a value of the second bit to control the light emission level or on/off operation of the LED 61.

TABLE 2

| 1ST BIT | 2ND BIT | BRIGHTNESS (LEVEL 1 < LEVEL 3) |
|---|---|---|
| 0 | 0 | TURN OFF |
| 0 | 1 | LIGHT EMISSION LEVEL 1 |
| 1 | 0 | LIGHT EMISSION LEVEL 2 |
| 1 | 1 | LIGHT EMISSION LEVEL 3 |

When both the first and second bits are zero, the LED driving circuit 63 turns off the LED 61.

When the first bit is one and the second bit is zero, the LED driving circuit 63 controls the LED 61 by the light emission level 2.

Figure 8:
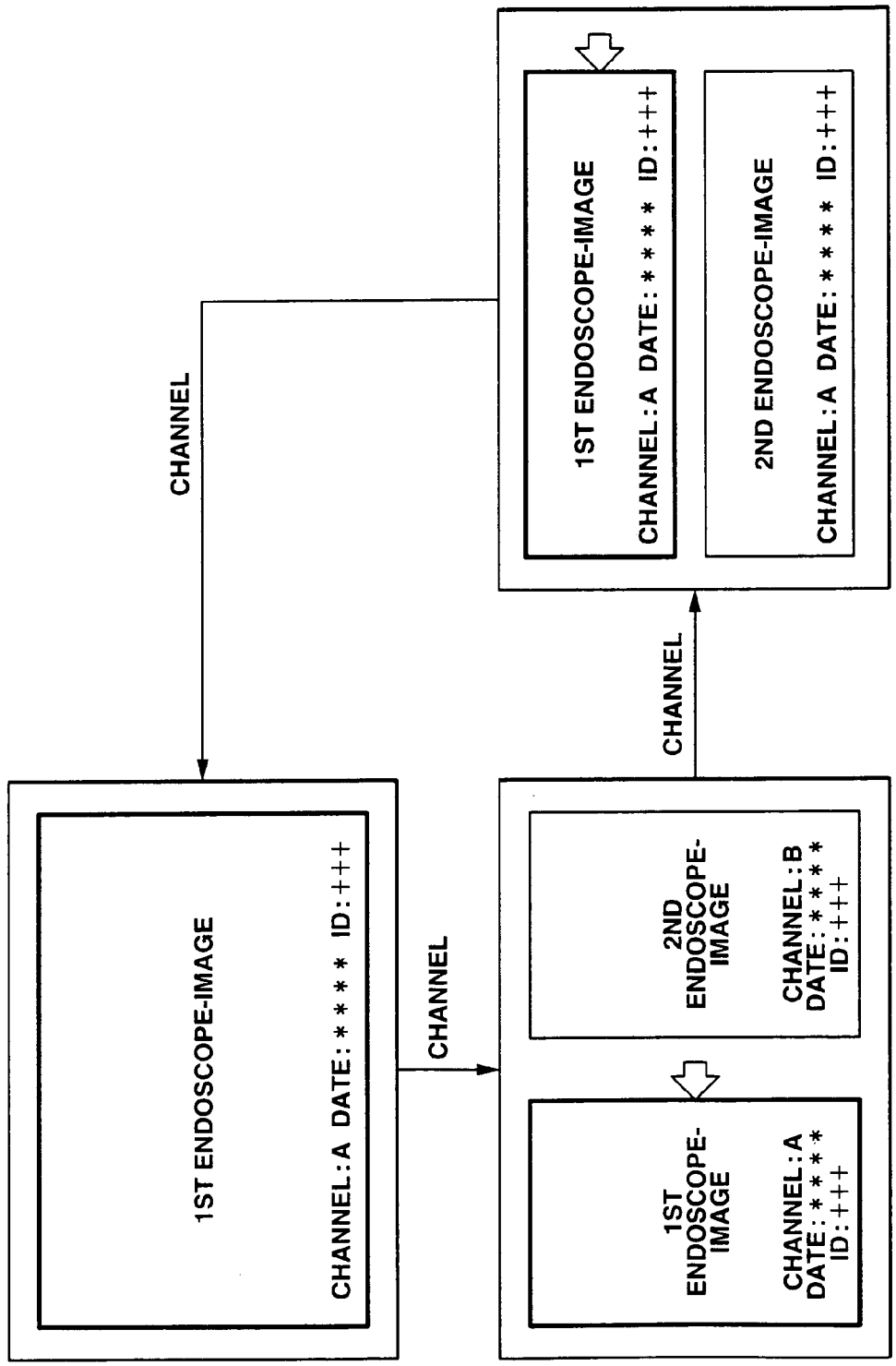
FIG. 8 is a diagram showing an example of a monitor display screen upon pressing a channel switch of a remote controller shown in FIG. 7.

When the parameter indicates the "press channel switch", the channel is operated as shown on the top in FIG. 8.

Referring to FIG. 8, the display screen of the monitor 13 displays the entire first endoscope image. An operator presses the channel switch 92a of the remote controller 11 once. Then, (the CPU 21a of) the endoscope control device 4 sends the character code for operating the channel to (the CPU 81a of) the endoscope switching device 3. (The CPU 81a of) the endoscope switching device 3 controls the image combining circuit 73 to combine the video signals from the first endoscope device 2A and the second endoscope device 2B, thereby simultaneously displaying the first and second endoscope images in the horizontal direction. Thus, the combined image signal is created. The created combined image signal is inputted to the video signal processing circuit 22 of the endoscope control device 4, is subjected to various signal processing, and is outputted to the monitor 13. As shown on the left bottom in FIG. 8, the first and second endoscope images are simultaneously displayed in the horizontal direction.

The operator presses, one more time, the channel switch 92a of the remote controller 11. Then, in the above-mentioned operation, the video signals from the first endoscope device 2A and the second endoscope device 2B are combined so as to simultaneously display the first and second endoscope images in the vertical direction. Thus, the first and second endoscope images are displayed on the display screen of the monitor 13 as shown on the right bottom in FIG. 8.

Further, the operator presses, one more time, the channel switch 92a of the remote controller 11, the indication returns the display of the original first endoscope image on the entire screen as shown on the top in FIG. 8.

On the bottom of the endoscope images, a channel name, date, and ID are displayed. In the case of combining the image, selecting and display means for identifying the desired endoscope device as the control target displays a display frame of the corresponding endoscope image by a bold-line frame and an arrow (outline arrow in the drawing).

In the display operation on the entire screen shown on the top in FIG. 8, the second endoscope image is displayed, in place of the first endoscope image. In the case of the combined image (displayed by division) shown on the left bottom in FIG. 8 or right bottom in FIG. 8, when the parameter indicates "press control switch", the selecting operation is executed as shown in FIG. 9.

Figure 9:
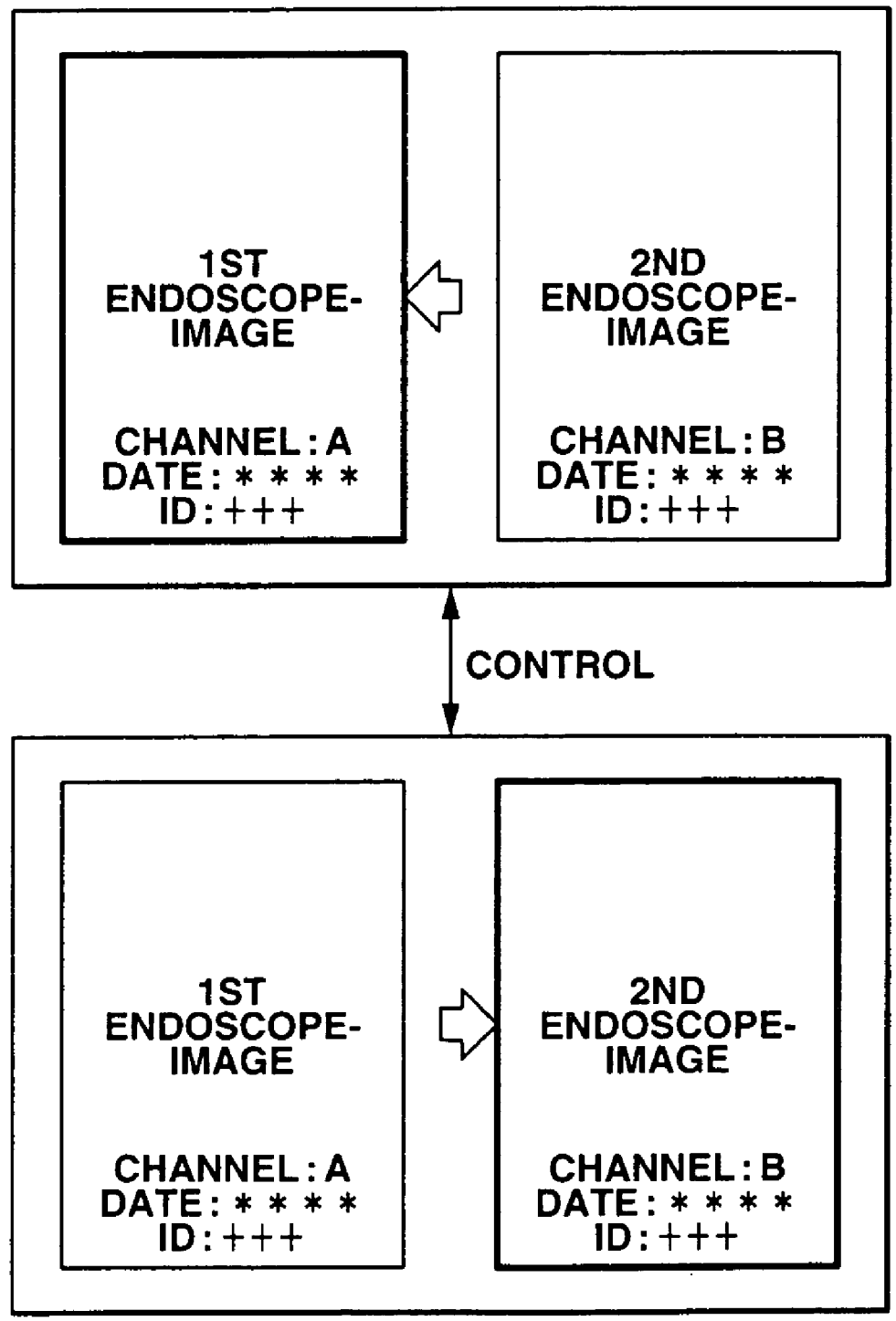
FIG. 9 is a diagram showing an example of a monitor display screen upon pressing a control switch of a remote controller shown in FIG. 7.

As shown on the top in FIG. 9, the display screen of the monitor 13 is simultaneously displayed in the horizontal direction, similarly to the left bottom in FIG. 8. In this case, on the top in FIG. 9, the remote controller 11 is operated for the first endoscope device 2A which obtains the first endoscope image as the control target.

The operator presses the control switch 92b of the remote controller 11 once. Then, (the CPU 21a of) the endoscope control device 4 sends the character code for control operation to (the CPU 81a of) the endoscope switching device 3 so as to control the selected second endoscope device 2B. Then, (the CPU 81a of) the endoscope switching device 3 distributes the command to operate the remote controller 11 for the second endoscope device 2B.

Then, (the CPU 21a of) the endoscope control device 4 controls the video signal processing circuit 22 as shown on the bottom in FIG. 9 so that the second endoscope image is displayed by the bold-line frame to operate the remote controller 11 to the second endoscope device 2B and so that the second endoscope image is subjected to image processing as shown by the arrow (outline arrow in FIG. 9).

Further, the operator presses, one more time, the control switch 92b of the remote controller 11. Then, in the above-mentioned operation, the remote controller 11 is operated for the original first endoscope device 2A and the indication returns to the original display screen as shown on the top in FIG. 9.

According to the first embodiment, for a brief description, as the 1st to N-th endoscope devices 2, the first endoscope device 2A and the second endoscope device 2B are connected to the endoscope switching device 3.

However, when the three or more endoscope devices are connected to the endoscope switching device 3 as shown in FIG. 1, the combined image (displayed by division, not shown) is divided into four or more as an even number in the endoscope system 1. In this case, when the number of endoscope devices is odd, one display screen is a blue (or gray) one.

Consequently, the endoscope system 1 according to the first embodiment selectively or simultaneously displays a plurality of endoscope image. In the case of simultaneous display, the desired endoscope device is controlled.

Second Embodiment

Figure 10:
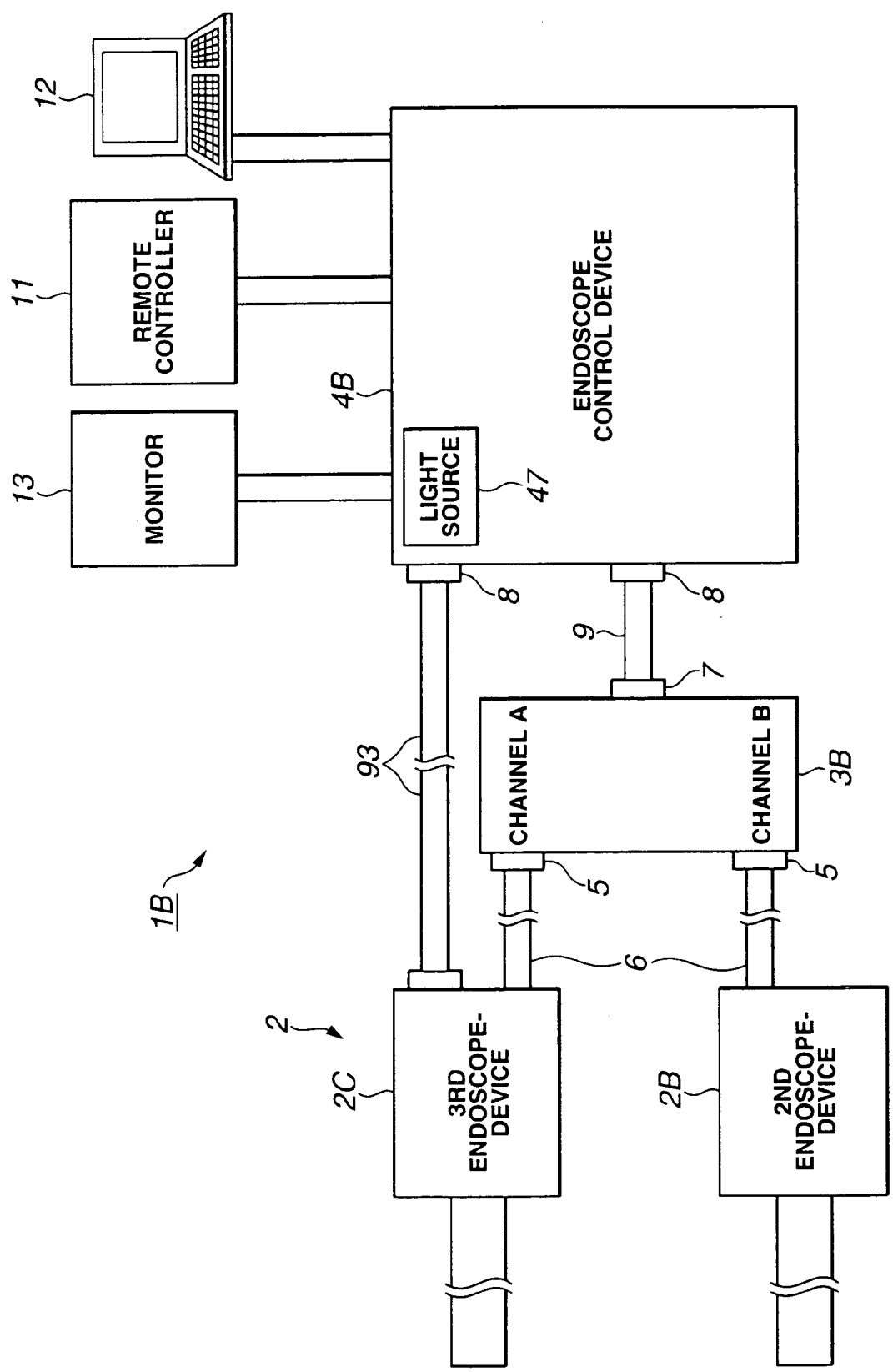
FIG. 10 is a diagram showing the entire structure of an endoscope system according to a second embodiment.
Figure 11:
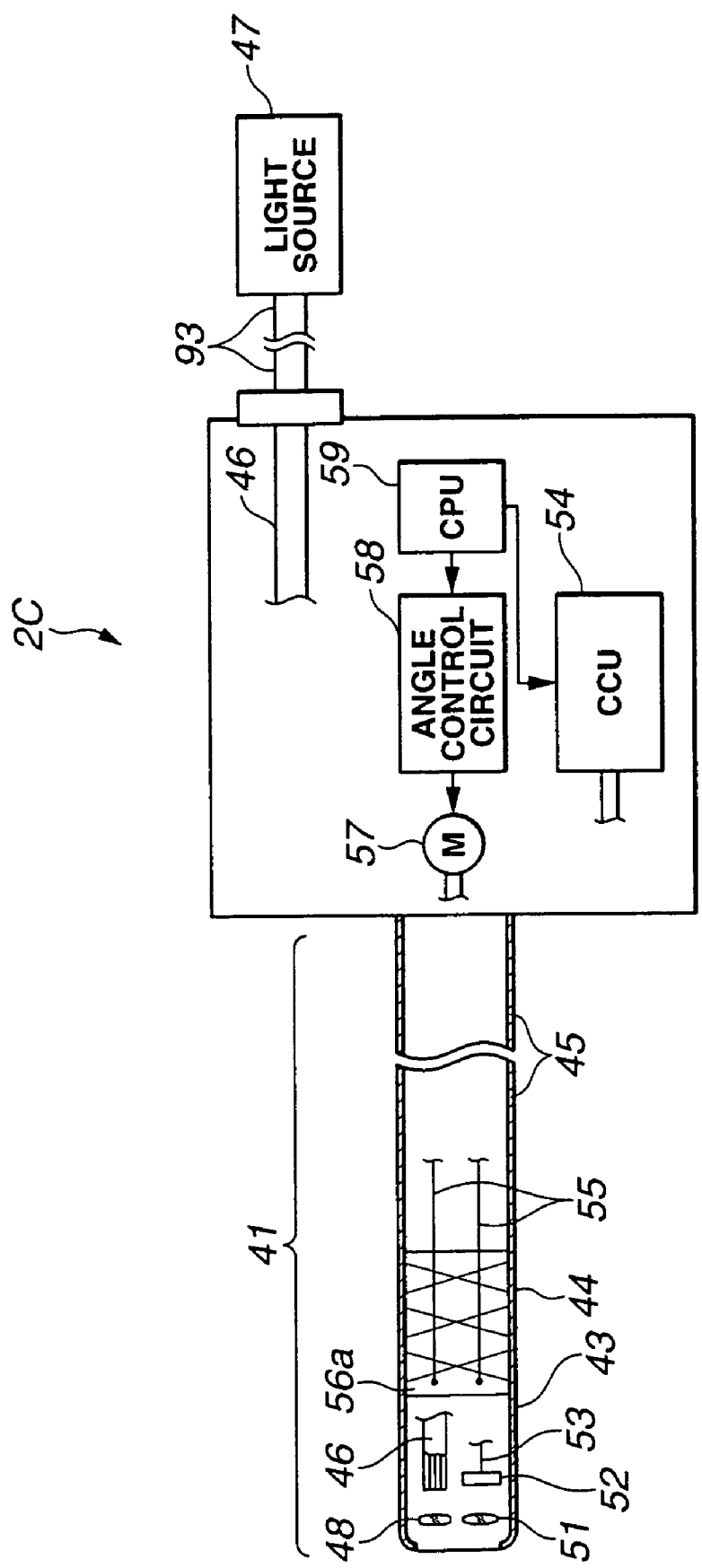
FIG. 11 is an explanatory diagram showing the inner structure of a third endoscope device.

FIGS. 10 and 11 show a second embodiment of the present invention.

According to the second embodiment, the endoscope control device 4 has a light source, and illumination light from the light source is supplied to the third endoscope device. The structure except for the foregoing according to the second embodiment is the same as that according to the first embodiment, a description thereof is omitted, and the same reference numerals denote the same components.

Referring to FIG. 10, an endoscope system 1B according to the second embodiment comprises: an endoscope control device 4B having the light source 47; and a third endoscope device 2C which receives the illumination light via a light cable 93 from the endoscope control device 4B. Referring to FIG. 11, in the third endoscope device 2C, the illumination light is transmitted to the light guide 46 from the endoscope control device 4B via the light guide cable 93.

Consequently, the third endoscope device 2C does not need the illumination light for monitoring, the light source 47 is easily turned on/off by arranging the light source 47 in the endoscope control device 4B.

The structure other than the foregoing is the same as that according to the first embodiment and therefore a description thereof is omitted.

Thus, the endoscope system 1B according to the second embodiment has the same advantages as those according to the first embodiment, and can correspond to the case in which the illumination light for monitoring is not necessary.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising:
   an image combining unit to which a plurality of endoscope devices are connected by wire, the image combining unit being configured to combine video signals outputted from each of the plurality of endoscope devices and to simultaneously display a plurality of endoscope images on a monitor;

a selecting unit configured to select a desired endoscope device of the plurality of endoscope devices as a control target, wherein the endoscope device selected as the control target is sensitive to one or more commands, and the endoscope devices not selected as the control target are insensitive to said one or more commands; and a selecting and displaying portion configured to identify the endoscope device selected as the control target;

wherein the selecting and display portion, in order to distinguish the endoscope device selected as the control target and set to be sensitive to said one or more commands by the selecting unit, displays the endoscope image obtained by the selected endoscope device in a bold-line frame.

2. An endoscope system according to claim 1 wherein the selecting and display portion is an arrow which indicates the endoscope image obtained by the selected endoscope device.

3. An endoscope system according to claim 1, wherein the image combining unit comprises a frame memory which temporarily stores the video signals outputted from the plurality of endoscope devices and a pixel combining unit which combines the video signal stored in the frame memory for every pixel.

4. An endoscope system according to claim 3, wherein the pixel combining unit comprises: a memory control circuit which generates a signal for selling valid/invalid of the video signal, an address generating circuit which generates an address signal of the frame memory to which valid/invalid is set by the memory control circuit; and a pixel combining and calculating circuit which combines the video signal stored in the frame memory for every pixel based on the address signal from the address generating circuit and the signal from the memory control circuit.

5. An endoscope system according to claim 1, wherein the image combining unit comprises a frame memory which temporarily stores the video signals outputted from the plurality of endoscope devices and a pixel combining unit which combines the video signal stored in the frame memory for every pixel.

6. An endoscope system according to claim 1, wherein the image combining unit comprises a frame memory which temporarily stores the video signals outputted from the plurality of endoscope devices and a pixel combining unit which combines the video signal stored in the frame memory for every pixel.

7. An endoscope system according to claim 1, wherein the image combining unit creates a combined image signal which displays the plurality of endoscope images in the horizontal direction.

8. An endoscope system according to claim 1, wherein the image combining unit creates a combined image signal which displays the plurality of endoscope images in the horizontal direction.

9. An endoscope system according to claim 1, wherein the image combining unit creates a combined image signal which displays the plurality of endoscope images in the horizontal direction.

10. An endoscope system according to claim 1, wherein the image combining unit creates a combined image signal which displays the plurality of endoscope images in the vertical direction.

11. An endoscope system according to claim 1, wherein the image combining unit creates a combined image signal which displays the plurality of endoscope images in the vertical direction.

12. An endoscope system according to claim 1, wherein the image combining unit creates a combined image signal which displays the plurality of endoscope images in the vertical direction.

13. An endoscope system, comprising:
an endoscope switching device: including; a plurality of connector portions to which a plurality of endoscope devices are connectable by wire;
a frame memory which temporarily stores image signals sent from each of the endoscope devices connected by wire;
an image combining section which combines the signals stored in the frame memory so that a plurality of endoscope images can be simultaneously displayed;
a switching device control unit which control the image combining section, wherein the switching device switches only a selected endoscopic device of the plurality of endoscope devices, according to a received character code for control operation, to be sensitive to one or more commands, while keeping unselected endoscope devices insensitive to said one or more commands, and distributes a received control command based on the received character code to each of the connected endoscope devices;
an endoscope control device, including:
a video signal processing circuit which is connected to the endoscope switching device and which processes image signals outputted from the endoscope switching device and outputs the processed image signals to a monitor;
a system control unit which sends the received control command and a character code generated based on the received control command to the endoscope switching device, sends the character code for control operation to a the switching device control unit of the endoscope switching device based on a received operation command so that the selected one of the plurality of connected endoscope devices becomes sensitive to said one or more commands, and controls the video signal processing circuit so as to display the endoscope image from the selected endoscope device, which is displayed on the monitor, in a bold-line frame to indicate that the selected endoscope device is sensitive to said one or more commands; and
an endoscope operation device which selects one of the plurality of endoscope devices connected to the endoscope switching device, which is to be sensitive to said one or more commands, sends to the endoscope control device the operation command for switching to the selected endoscope device to be sensitive to said one or more commands, and sends the control command to the endoscope control device, to the endoscope switching device via the endoscope control device, and to the connected endoscope devices via the endoscope switching device.

14. An endoscope system comprising:
an image combining unit to which a plurality of endoscope devices are connected by wire, the image combining unit being configured to combine video signals outputted from each of the plurality of endoscope devices, and to simultaneously display a plurality of endoscope images on a monitor;
an endoscope switching device, to which a plurality of endoscope devices are simultaneously connected by wire and which combines video signals outputted from the plurality of endoscope devices;

a selecting unit configured to select a desired one of the plurality of endoscope devices as a control target, and bring the endoscope device which is insensitive to one or more commands until it is selected to be sensitive to said one or more commands by the selection; and a selecting and displaying portion configured to identify the endoscope device selected as the control target;

wherein the selecting and display portion, in order to distinguish the endoscope device selected as the control target and selected to be sensitive to said one or more commands by the selecting unit from the other endoscope devices, displays the endoscope image obtained by the selected endoscope device in a highlighted frame.

15. An endoscope system according to claim 14, further comprising an endoscope control device connected to the endoscope switching device, the endoscope control device being configured to control an angle control circuit or the like of the endoscope device selected as the control target by the selecting unit.

* * * * *